(12) United States Patent
Dahl et al.

(10) Patent No.: US 11,370,799 B2
(45) Date of Patent: Jun. 28, 2022

(54) METHODS FOR THE PREPARATION OF 1,3-BENZODIOXOLE HETEROCYCLIC COMPOUNDS

(71) Applicant: UNION therapeutics A/S, Hellerup (DK)

(72) Inventors: Allan Carsten Dahl, Ballerup (DK); Gitte Holm Jensen, Ballerup (DK); Tine Marianne Duus, Ballerup (DK)

(73) Assignee: Union therapeutics A/S, Hellerup (DK)

( * ) Notice: Subject to any disclaimer, the term of this patent is extended or adjusted under 35 U.S.C. 154(b) by 127 days.

(21) Appl. No.: 16/062,760

(22) PCT Filed: Dec. 16, 2016

(86) PCT No.: PCT/EP2016/081368
§ 371 (c)(1),
(2) Date: Jun. 15, 2018

(87) PCT Pub. No.: WO2017/103058
PCT Pub. Date: Jun. 22, 2017

(65) Prior Publication Data
US 2020/0262842 A1 Aug. 20, 2020

(30) Foreign Application Priority Data

Dec. 18, 2015 (EP) .................................. 15201053

(51) Int. Cl.
*C07D 495/10* (2006.01)

(52) U.S. Cl.
CPC ................................ *C07D 495/10* (2013.01)

(58) Field of Classification Search
USPC ...................................................... 546/280
See application file for complete search history.

(56) References Cited

U.S. PATENT DOCUMENTS

| | | |
|---|---|---|
| 6,716,987 B1 | 4/2004 | Ohshima |
| 8,338,431 B2 | 12/2012 | Bollu et al. |
| 8,980,905 B2 | 3/2015 | Nielsen |
| 9,273,064 B2 | 3/2016 | Nielsen |
| 9,637,499 B2 | 5/2017 | Nielsen |
| 9,908,894 B2 | 3/2018 | Metzler et al. |
| 11,220,514 B2 | 1/2022 | Dahl et al. |
| 2003/0203918 A1 | 10/2003 | Meade |
| 2005/0245750 A1 | 11/2005 | Atsumi |
| 2008/0015226 A1 | 1/2008 | Amari |
| 2010/0035908 A1 | 2/2010 | Felding |

FOREIGN PATENT DOCUMENTS

| | | | |
|---|---|---|---|
| JP | 2006/008522 A | 1/2008 | |
| JP | 2012/229192 A | 11/2012 | |
| WO | WO 2008/077404 A1 | 7/2008 | |
| WO | 2008/104175 A2 | 9/2008 | |
| WO | WO 2008/104175 A2 | 9/2008 | |
| WO | 2008104175 A3 | 1/2009 | |
| WO | WO 2011/160632 A1 | 12/2011 | |
| WO | WO 2014/096018 A1 | 6/2014 | |
| WO | WO 2015/197534 A2 | 12/2015 | |
| WO | WO-2015197534 A2 * | 12/2015 | ........... C07D 495/10 |
| WO | 2017/103058 A1 | 6/2017 | |
| WO | 2018234299 A1 | 12/2018 | |

OTHER PUBLICATIONS

Roberto Ballini et al . Zeolite HSZ-360 as a new reusable catalyst for direct acetylation of alcohols and penols under solventless conditions. (Year: 1998).*
Sperry, Jeffrey B. et al, "A Safe and Practical Procedure for the Difluoromethylation of Methyl 4-Hydroxy-3-iodobenzoate," Organic Process Research & Development, vol. 15, pp. 721-725 (2011).
Zafrani, Yossi et al, "Diethyl bromodifluoromethylphosphonate: a highly efficient and environmentally benign difluorocarbene precursor," Tetrahedron, vol. 65, pp. 5278-5283 (2009).
Zhang, Laijun et al, "2-Chloro-2,3-difluoroacetophenone: A Non-ODS-Based Difluorocarbene Precursor and its use in the Difluoromethylation of Phenol Derivatives," Journal Organic Chemistry, vol. 71, pp. 9845-9848 (1903).
Zheng, Ji et al, "Chlorodifluoromethyl phenyl sulfone: a novel non-ozone-depleting substance-based difluorocarbene reagent for O- and N-difluoromethylations," Chem. Commun., pp. 5149-5151 (2007).
International Search Report for International Application No. PCT/EP2016/081368, dated Feb. 22, 2017.
Written Opinion of the International Search Authority for International Application No. PCT/EP2016/081368.
Frey, Lisa F. et al., "Practical synthesis of a highly functionalized thiazole ketone," Tetrahedron, vol. 59, pp. 6363-6373 (2003).
Yanagisawa; Org. Process Res. Dev. 2011, 15, 376-381.
International Search Report and Written Opinion of ISA/EP dated Jan. 26, 2016, for PCT/EP2015/063942.
PubChem CID 54765967 (Jan. 23, 2012).
International Search Report and Written Opinion of the International Searching Authority for International Application No. PCT/EP18/066229 dated Oct. 15, 2018.

* cited by examiner

*Primary Examiner* — Zinna Northington Davis
(74) *Attorney, Agent, or Firm* — DLA Piper LLP (US)

(57) ABSTRACT

The present invention relates to novel methods for the preparation of 1,3-benzo-dioxole heterocyclic compounds and intermediates for the same. The compounds are useful as PDE4 inhibitors.

16 Claims, No Drawings

METHODS FOR THE PREPARATION OF 1,3-BENZODIOXOLE HETEROCYCLIC COMPOUNDS

This application is a national stage filing under 35 U.S.C. § 371 of International Application No. PCT/EP2016/081368, filed on Dec. 16, 2016, which claims priority of European Patent Application No. 15201053.4, filed Dec. 18, 2015. The contents of these applications are each incorporated herein by reference.

FIELD OF THE INVENTION

The present invention relates to novel methods for the preparation of 1,3-benzo-dioxole heterocyclic compounds and intermediates for the same. The compounds are useful as PDE4 inhibitors.

BACKGROUND OF THE INVENTION

WO 2011/160632 discloses benzodioxole and benzodioxepene heterocyclic compounds useful as PDE4 inhibitors as well as suitable methods for the preparation thereof.
WO 2008/104175 discloses benzodioxole and benzodioxepene heterocyclic compounds useful as PDE4 inhibitors as well as suitable methods for the preparation thereof.
WO 2008/077404 discloses substituted acetophenones useful as PDE4 inhibitors as well as suitable methods for the preparation thereof.
PCT/EP2015/063942, earliest priority date of 23 Jun. 2014, discloses methods for the preparation of 1,3-benzodioxole heterocyclic compounds.
Zafrani et al. *Tetrahedron* 65, 2009, pp 5278-5283, describes a method for the difluoromethylation of phenols and thiophenols.
Sperry et al *Org. Process Res. Dev.* 15, 2011, pp 721-725, also describes the difluoromethylation of phenols.
Frey et al. *Tetrahedron* 2003, 59, pp. 6363-6373 also describes the demethylation and difluoromethylation of phenols
Zhang et al. *J. Org. Chem.* 2006, 71, 9845-9848 also describes the difluoro-methylation of phenols.
Zheng et al. *Chem. Commun.* 2007, 5149-5151 also describes the difluoromethylation of phenols.

In the development of new drug candidates, it is highly desirable to have access to alternative methods for the preparation of the drug candidates, as some efficient small-scale synthesis may turn out to be difficult to up-scale to production scale quantities. Also, small-scale syntheses may involve reagents and solvents which are not feasible to utilize at a production scale level.

Hence, it is an object of the present invention to provide alternative methods for the preparation of 1,3-benzodioxole heterocyclic compounds of the type disclosed in WO 2011/160632 and PCT/EP2015/063942, insofar that such alternative methods provide advantages with respect to one or more features like the number of reactions steps, purity, yield, ease of purification, process economy, availability of starting materials and reagents, safety, predictability, etc.

Surprisingly, in step (2a) of the present invention, the yield is ≥80%, which by far surpasses the yield of 32% obtained in the deprotection of the phenol group in the method as described in WO 2011/160632. Further, the method as described in WO 2011/160632 relies on chromatography for the purification of the product, whereas the present method makes it possible to purify the product by simple unit operations easily scalable in a production plant.

Further, surprisingly, in step (3) of the present invention, the difluoromethyl group can now be introduced in a yield of ≥76% with or without isolating an intermediate salt. This surpasses the yield of 52% as obtained by the method as in described in WO 2011/160632. Further, the method as described in WO 2011/160632 relies on chromatography for the purification of the product, whereas the present method makes it possible to purify the product by very simple unit operations easily scalable in a production plant.

The improved yield and the easy scale up of the process of the present invention as compared to the method as described in WO 2011/160632, are quite surprising.

SUMMARY OF THE INVENTION

It has been found by the present inventors that the alternative method disclosed herein provides advantages over the known methods by a reduced number of steps, an improved overall chemical and volumetric yield and an accompanying reduced cost for the production.

Hence, the present invention provides a method for the preparation of 1,3-benzo-dioxole compounds, e.g. a compound of formula (I).

Also within the scope of the invention are intermediates used in the foregoing method for preparing compounds of formula (I).

DETAILED DISCLOSURE OF THE INVENTION

In a first aspect, the present invention relates to a method for the preparation of a compound of formula (I)

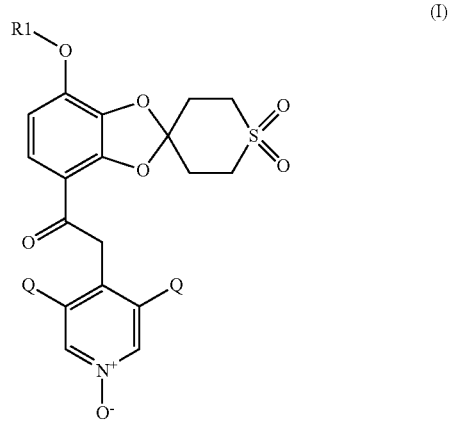

wherein $R_1$ is selected from $CHF_2$ and $CF_3$, and Q is selected from chloro, bromo and fluoro.

In the compound of formula (I), $R_1$ is typically $CHF_2$. Q is typically selected from chloro, bromo and fluoro, preferably chloro, where the Q's preferably are the same. In one embodiment, both Q's are chloro.

DEFINITIONS

The term "$C_{1-6}$-alkyl" is intended to mean a saturated, straight or branched hydrocarbon chain having from one to six carbon atoms, including methyl, ethyl, propyl, isopropyl, butyl, isobutyl, secondary butyl, tertiary butyl, pentyl, isopentyl, neopentyl, tertiary pentyl, hexyl and isohexyl. In some embodiments, "$C_{1-6}$-alkyl" is a $C_{1-4}$-alkyl group, e.g. methyl, ethyl, propyl, isopropyl, butyl, isobutyl, secondary butyl and tertiary butyl. Correspondingly, "$C_{1-3}$-alkyl" includes methyl, ethyl, propyl and isopropyl.

The term "halogen" is intended to mean one of fluoro, chloro, bromo and iodo. In one embodiment, the term "halogen" designates fluoro or chloro. In another embodiment, the term "halogen" designates chloro.

The term "aryl" is intended to mean a carbocyclic aromatic ring system derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, and biphenyl. Preferred "aryl" is phenyl, naphthyl or indanyl, in particular phenyl, unless otherwise stated.

The term "arylalkyl" is intended to mean an aryl radical as defined above covalently joined to an alkyl group, e.g. benzyl.

METHODS OF PREPARATION

It appears that the method provides advantages over the known methods by relying on cheap starting materials, ease of the production method, and increasing yields in the reactions.

Step (1)

The method for the preparation of a compound of the formula (I) includes the formation of a compound of the formula (IV) which is obtained by reacting a compound of formula (II)

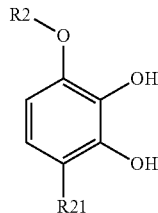

(II)

wherein $R_2$ is selected from hydrogen, $C_{1-6}$-alkyl and arylalkyl, $R_{21}$ is selected from hydrogen and $C(O)R_{22}$, and $R_{22}$ is selected from hydrogen and $C_{1-6}$-alkyl; with a compound of formula (III)

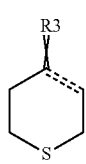

(III)

wherein " ⋊⋉ " represents a single bond, a double bond or two single bonds, and when " ⋊⋉ " represents a double bond or two single bonds, "═" is a single bond, and when " ⋊⋉ " represents a single bond, "═" is a double bond; $R_3$ represents oxygen when " ⋊⋉ " represents a double bond and $R_3$ represents O—$C_{1-6}$-alkyl when " ⋊⋉ " represents a single bond or two single bonds; in the presence of an acid catalyst to form a compound of formula (IV)

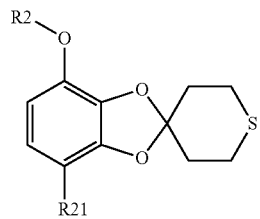

(IV)

wherein $R_2$ and $R_{21}$ is as defined above.

The acid catalyst is typically in form of a silicate mineral. The silicate mineral is typically selected from Montmorillonite K10, Montmorillonite K30, Montmorillonite KSF, Zeolite HSZ-341NHA, Zeolite HSZ-331NHA, Zeolite HSZ-350HUA and Zeolite HSZ-360HUA. In one embodiment, the silicate mineral is selected from Montmorillonite K10 and Zeolite HSZ-360HUA. In another embodiment, the silicate mineral is Montmorillonite K10.

The compound of formula (III) is typically selected from

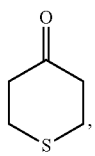

(IIIa)

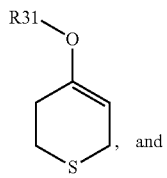

(IIIb)

and

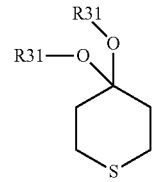

(IIIc)

wherein $R_{31}$ represents $C_{1-6}$-alkyl. In one embodiment, the compound of formula (III) is selected from the compounds of formula (IIIa), and formula (IIIb), wherein $R_{31}$ represents methyl. In another embodiment, the compound of formula (III) is tetrahydrothiopyran-4-one.

The ratio between the silicate mineral and compound of formula (II) may have influence on the conversion and filtration-time. Hence, it is typically preferred to have an amount of the mineral of 25%-w/w to 500%-w/w compared to the compound of formula (II). In particular the amount of mineral should be of 25%-w/w to 75%-w/w. preferably in the range 45%-w/w to 55%-w/w.

The reaction is typically conducted in toluene, benzene, 2-Methyl-THF (2-methyl-tetrahydrofuran), EtOAc (ethyl acetate), xylenes, heptane, octane, chlorbenzene and dichlorbenzene. In one embodiment, the solvent is toluene.

The reaction is typically conducted at a temperature above 80° C. in order to promote the reaction. Hence, it is typically preferred that the temperature is in the range of 80-200° C., such as in the range of 100-160° C., especially at 105-115° C. In one embodiment, the reaction is performed at reflux of the reaction mixture. The reaction is typically allowed to proceed for 4-96 hours, such 24-84 hours, especially 48-84 hours.

The resulting compound of formula (IV) may be recovered by conventional means, known to those skilled in the art, e.g. by aqueous workup followed by extraction and finally precipitation and filtration.

In one embodiment of the invention, the compound of formula (II) is wherein $R_2$ is selected from hydrogen or methyl and $R_{21}$ is selected from hydrogen, $COCH_3$ or COOH. In another embodiment, the compound of formula (II) is 1-(2,3-dihydroxy-4-methoxyphenyl)ethanone.

In one embodiment of the invention, the compound of formula (III) is tetrahydrothiopyran-4-one.

In one embodiment of the invention, the compound of formula (IV) is wherein $R_2$ is hydrogen, methyl, ethyl, propyl, isopropyl, isobutyl, secondary butyl, tertiary butyl or benzyl, and $R_{21}$ is selected from hydrogen, $COCH_3$ or COOH. In another embodiment the compound of formula (IV) is wherein $R_2$ is methyl and $R_{21}$ is $COCH_3$.

Step (2a)

The compound of the formula (IV)

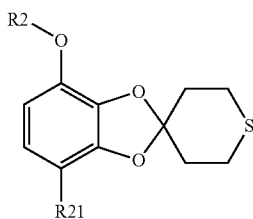

(IV)

wherein $R_2$ and $R_{21}$ is as defined above, is converted to a compound of formula (VI)

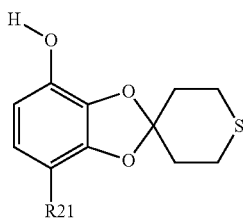

(VI)

wherein $R_{21}$ is defined above by deprotecting the phenol moiety.

This may be done by reacting the compound of formula (IV) with an aromatic or aliphatic thiol in combination with a base.

The aromatic thiol may be e.g., but is not limited to, benzenethiol, 4-methylbenzene-thiol, 3,5-dimethylbenzenethiol, 2,5-dimethylbenzenethiol, 4-isopropylbenzenethiol, or 5-tert-butyl-2-methyl-benzenethiol. In one embodiment, the aromatic thiol is 5-tert-butyl-2-methyl-benzenethiol.

The aliphatic thiol may be e.g, but is not limited to, 1-dodecanethiol, 1-tetra-decanethiol, 1-hexadecanethiol, or tert-dodecanethiol. In one embodiment, the aliphatic thiol is 1-dodecanethiol.

The deprotection of the phenol group in step (2a) may be conducted using various solvents, e.g. selected from DMF (N,N-dimethylformamide), NMP (N-methyl-pyrrolidone), DMSO (dimethyl sulfoxide), methanol, or ethanol and mixtures hereof. In one embodiment, the solvent is DMF. In another embodiment, the solvent is a mixture of DMF and methanol.

The deprotection of the phenol group is performed in the presence of a base, e.g. selected from $K_2CO_3$, $Na_2CO_3$, $KHCO_3$, $NaHCO_3$, $CsCO_3$, TEA (triethylamine), potassium tert-butoxide, tert-BuOLi (lithium tert-butoxide), sodium methoxide, sodium ethoxide, and DIPEA (N,N-diisopropylethylamine). In one embodiment, the base is $K_2CO_3$. In another embodiment, the base is sodium methoxide.

The reaction is typically conducted at a temperature in the range of 50-120° C., such as in the range of 70-100° C. The reaction is typically allowed to proceed for 2-36 hours, such as 3-24 hours. The reaction is typically allowed to proceed until the conversion is ≥198%.

The resulting compound of formula (VI) may be recovered by conventional means, known to those skilled in the art, e.g. by aqueous workup followed by extraction and finally precipitation and filtration.

In one embodiment of the invention, the compound of formula (VI) is wherein $R_{21}$ is $C(O)R_{22}$, and $R_{22}$ is selected from hydrogen and $C_{1-6}$-alkyl. In another embodiment the compound of formula (VI) is 1-(7-hydroxyspiro[1,3-benzodioxole-2,4'-tetrahydro-thiopyran]-4-yl)ethanone.

Step (2b)

In step (2b) the compound of formula (VI) is reacted with aqueous $N(Bu)_4{}^+OH^-$ to form a compound of formula (VII)

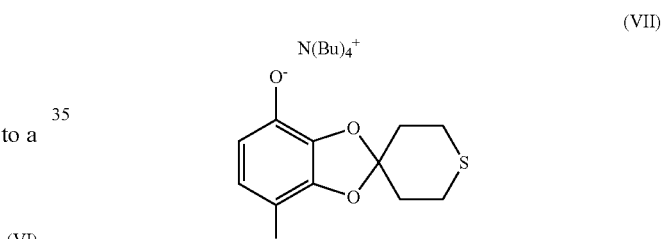

(VII)

wherein $R_{21}$ is as defined above.

The mixture is typically heated to a temperature in the range of 20-80° C., such as 55-65° C., until all has dissolved.

The resulting solution is typically washed with a solution of sodium chloride in water by stirring at a temperature in the range of 20-80° C., such as 55-65° C. for ≥20 min. Subsequently adding a mixture of water and sodium chloride followed by cooling of the mixture from ≥35° C. to 0-20° C., e.g. 5° C. over a period of 1-24 hours, such as 1-4 hours, causes the TBA (tetrabutylammonium) salt to precipitate. The TBA salt is isolated e.g. by filtration and dried.

Step (3)

The compound of formula (IX)

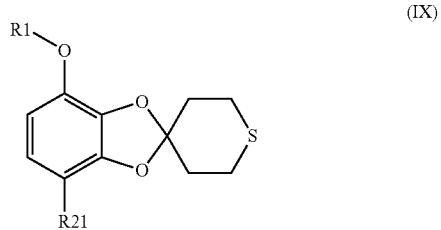

(IX)

wherein $R_1$ and $R_{21}$ are as defined above, may be obtained by alkylating the resulting compound of formula (VII)

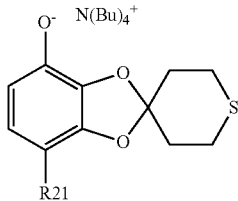
(VII)

wherein $R_{21}$ is as defined above, by reacting with a hydrochlorofluorocarbon reagent,

(VIII)

wherein $R_1$ is as defined above.

The alkylation may be conducted using one of various possible reagents, such as various hydrochlorofluorocarbon gases. In one embodiment, the alkylation reaction is conducted using chlorodifluoromethane in an aprotic polar solvent, e.g. selected from DMF (N,N-dimethylformamide), NMP (N-methylpyrolidone), DMI (1,3-dimethyl-2-imidazolidinone), DMSO (dimethyl sulfoxide), EtOAc (ethyl acetate), MeCN (acetonitrile) and THF (tetrahydrofuran), and mixtures hereof. In one preferred embodiment, the aprotic solvent is selected from DMF and NMP. In a particular embodiment, the reaction is conducted using chlorodifluoromethane in DMF.

The reaction is typically conducted at a temperature in the range of 40-120° C., such as in the range of 50-70° C. The reaction is typically allowed to proceed until ≤4% of the phenol is left in the reaction mixture.

The resulting compound of formula (IX) may be recovered by conventional means, known to those skilled in the art, e.g. by aqueous workup followed by precipitation and subsequently filtration.

In one embodiment of the invention, the compound of the formula (IX) is 1-[7-(difluoromethoxy)spiro[1,3-benzodioxole-2,4'-tetrahydrothiopyran]-4-yl]ethanone.

Alternative step (2b+3)

Alternatively, the compound of formula (IX),

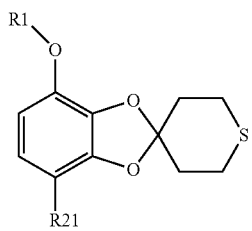
(IX)

wherein $R_1$ and $R_{21}$ are as defined above, may be obtained from the compound of formula (VI),

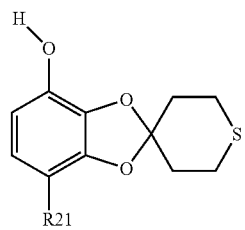
(VI)

wherein $R_{21}$ is defined above, without forming the intermediate salt of the formula (VII), by using a difluorocarbene source in a polar solvent in the presence of a base.

The difluorocarbene source is selected from e.g., but not limited to, sodium chlorodifluoroacetate, diethyl bromodifluoromethylphosphonate, chlorodifluoromethyl phenyl sulfone, and 2-chloro-2,2-difluoroacetophenone. Those skilled in the art can easily choose other suitable analogous of the mentioned difluorocarbene sources. In one embodiment, the difluorocarbene source is sodium chlorodifluoroacetate. In another embodiment, the difluorocarbene source is diethyl bromodifluoromethylphosphonate.

The reaction is performed in a solvent selected from e.g. NMP (N-methylpyrolidone), DMI (1,3-dimethyl-2-imidazolidinone), DMSO (dimethyl sulfoxide), EtOAc (ethyl acetate), MeCN (acetonitrile), THF (tetrahydrofuran), ethanol, methanol, water, and mixtures hereof. In one embodiment, the solvent is a mixture of water and DMF. In another embodiment, the solvent is a mixture of water and acetonitrile.

The reaction is performed in the presence of a base selected from e.g. $K_2CO_3$, $Na_2CO_3$, $KHCO_3$, $NaHCO_3$, $CsCO_3$, TEA (triethylamine), tert-BuOLi (lithium tert-butoxide), sodium methoxide, sodium ethoxide, DIPEA (N,N-diisopropylethylamine), KOH, NaOH, LiOH. In one embodiment, the base is $K_2CO_3$. In another embodiment, the base is NaOH.

The reaction is typically conducted at a temperature in the range of 0-120° C., such as 6-115° C. In one embodiment, the reaction is performed at 6-20° C. using diethyl bromodifluoromethylphosphonate as difluorocarbene source. In another embodiment, the reaction is performed at ambient temperature to 111° C. using sodium chloro-difluoroacetate as difluorocarbene source.

In one embodiment of the invention, the compound of the formula (IX) is 1-[7-(difluoromethoxy)spiro[1,3-benzodioxole-2,4'-tetrahydrothiopyran]-4-yl]ethanone.

The resulting compound of formula (IX), wherein $R_1$ and $R_{21}$ are as defined above, may be recovered by conventional means, known to those skilled in the art, e.g. by aqueous workup followed by precipitation and subsequently filtration.

Step (4)

In step (4), the compound of formula (IX) is reacted with a pyridine compound of formula (X)

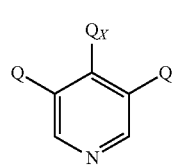
(X)

wherein Q is as defined above and $Q_x$ is selected from chloro, bromo, fluoro and iodo to form a compound of formula (XI)

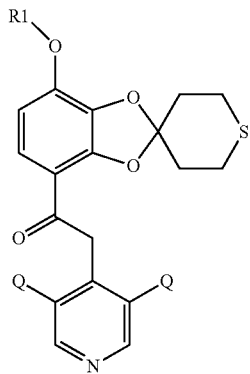

(XI)

wherein $R_1$ and Q are as defined above.

The pyridine coupling in step (4), is typically conducted in an polar solvent, e.g. selected from DMF (N,N-dimethylformamide), NMP (N-methylpyrrolidone), DMI (1,3-dimethyl-2-imidazolidinone), DMSO (dimethyl sulfoxide), MeCN (acetonitrile) and THF (tetrahydrofuran), and mixtures hereof, in the presence of a base, e.g. selected from tert-BuOK (potassium tert-butoxide), tert-BuOLi (lithium tert-butoxide), tert-BuONa (sodium tert-butoxide), sodium or potassium methoxide, sodium or potassium ethoxide, $K_2CO_3$, $Na_2CO_3$, $KHCO_3$, $NaHCO_3$, $Et_3N$ (triethylamine) and DIPEA (N,N-diisopropylethylamine). In one embodiment, the solvent is DMF and the base is tert-BuOK.

Usually two equivalents or more of the base is used relative to the compound of the formula (IX), such as where the molar ratio (base)/(formula IX) is from 5:1 to 2:1, e.g. from 3:1 to 2:1, especially from 2.4:1 to 2.7:1.

The reaction in step (4) is typically conducted at a temperature of 0-40° C., such as 5-25° C.

In one embodiment of the invention, the compound of formula (X) is 3,4,5-trichloro-pyridine.

In one embodiment of the invention, the compound of formula (XI) is 2-(3,5-dichloro-4-pyridyl)-1-[7-(difluoromethoxy)spiro[1,3-benzodioxole-2,4'-tetrahydrothiopyran]-4-yl]ethanone.

During the reaction, an impurity of formula (XII) is formed in considerable amounts.

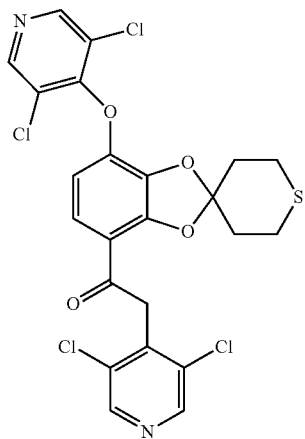

(XII)

This impurity is purged from the product by crystallising the product from a solvent selected from e.g. dimethylformamide (DMF), ethanol, methanol, ethyl acetate, hexane, heptane, and mixtures thereof. In one embodiment of the invention, the solvent is a mixture of ethyl acetate and ethanol.

Step (5)

The oxidation of the resulting compound of formula (XI) is conducted to form the compound of formula (I)

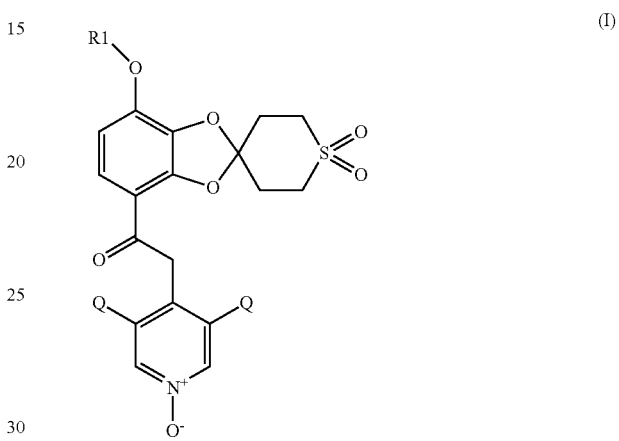

(I)

wherein $R_1$ and Q are as defined above, by reacting said compound of formula (XI) with an oxidation reagent.

The oxidation reagent is typically selected from PAA (peracetic acid) in AcOH (acetic acid), and $H_2O_2$ (aq) in formic acid or acetic acid. In one preferred embodiment, the oxidation reagent is PAA in AcOH. In one embodiment the amount of PAA used relative to (XI) (molar ratio) is typically 3 to 6, such as 3.8 to 4.2. The oxidation reagent is typically slowly added over a period of 1-8 hours, such as 3-5 hours, keeping the temperature in the range of 15-100° C., such as in the range of 15-50° C., especially in the range of 15-40° C.

The reaction is typically conducted at a temperature in the range of 30-70° C., such as 40-60° C., especially 48-52° C., and stirred for 3-48 hours, such as 16-24 hours.

Purification of the Compound of Formula (I)

The resulting crude product of formula (I) may advantageously be purified by crystallization, precipitation, chromatography or the like.

In one embodiment the resulting crude product of formula (I) is crystallized from a mixture of water and EtOH (ethanol), and isolated by filtration and dried.

The Intermediates

In another aspect, the present invention relates to intermediates which are useful in the preparations of a compound of the formula (I) wherein $R_1$ is selected from $CHF_2$ and $CF_3$, and Q is selected from chloro, bromo and fluoro.

In one embodiment the invention relates to the intermediate compound of formula (VI)

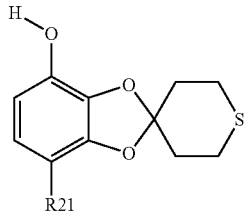

(VI)

wherein $R_{21}$ is selected from hydrogen and $C(O)R_{22}$, and $R_{22}$ is selected from hydrogen and $C_{1-6}$-alkyl. In another embodiment, the intermediate compound of formula (VI) is 1-(7-hydroxyspiro[1,3-benzodioxole-2,4'-tetrahydrothiopyran]-4-yl)ethanone.

In another embodiment the invention relates to the intermediate compound of formula (VII)

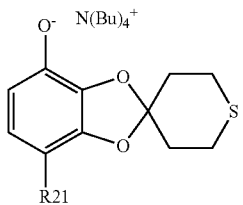

(VII)

wherein $R_{21}$ is selected from hydrogen and $C(O)R_{22}$, and $R_{22}$ is selected from hydrogen and $C_{1-6}$-alkyl. In another embodiment, the intermediate compound of formula (VII) is tetrabutylammonium 7-acetylspiro[1,3-benzodioxole-2,4'-tetrahydro-ithiopyran]-4-olate.

In another embodiment the invention relates to the intermediate compound of formula (IX)

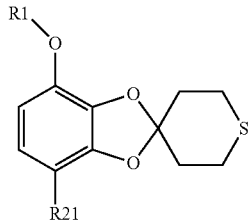

(IX)

wherein $R_1$ is selected from $CHF_2$ and $CF_3$, and $R_{21}$ is selected from hydrogen and $C(O)R_{22}$, and $R_{22}$ is selected from hydrogen and $C_{1-6}$-alkyl.

In another embodiment $R_1$ represents $CHF_2$, and $R_{21}$ is $C(O)R_{22}$ and $R_{22}$ is selected from hydrogen and $C_{1-6}$-alkyl. In another embodiment, the intermediate compound of formula (IX) is 1-[7-(difluoromethoxy)spiro[1,3-benzodioxole-2,4'-tetrahydro-thiopyran]-4-yl]ethanone.

EXPERIMENTALS

Methods and Reagents

All chemicals and reagents used were available from commercial sources.

$^1H$ nuclear magnetic resonance (NMR) spectra were recorded at the indicated magnetic field and chemical shift values ($\delta$, in ppm) are quoted in the specified solvent relative to tetramethylsilane ($\delta$=0.00).

HPLC: Column: Aeris Peptide 3.6 μm XB-C18, 100×4.6 mm, the eluent was a gradient of A: 10% MeCN; 90% H2O; 0.1% TFA and B: 90% MeCN; 10% H2O; 0.1% TFA, column temperature: 35° C., UV detection at 220 nm, flow rate: 1.5 mL/min. The following gradients of the eluents were used:

Gradient steps 2a, 2b, 3, and 5

| Time (min) | % A | % B |
|---|---|---|
| 0 | 85 | 15 |
| 8 | 20 | 80 |
| 10 | 20 | 80 |
| 10 | 85 | 15 |
| 12.2 | 85 | 15 |

Gradient Step 4

| Time (min) | % A | % B |
|---|---|---|
| 0 | 75 | 25 |
| 5 | 20 | 80 |
| 12.2 | 20 | 80 |
| 12.2 | 75 | 25 |
| 13.2 | 75 | 25 |

Example 1

Step (1): Preparation of 1-(7-methoxyspiro[1,3-benzodioxole-2,4'-tetrahydro-thiopyran]-4-yl)ethanone A reactor was charged with 1-(2,3-dihydroxy-4-methoxyphenyl)ethanone (60.0 kg, 329 mol), tetrahydrothiopyran-4-one (37.2 kg, 320 mol), Montmorillonite K 10 (30.0 kg), and toluene (720.0 L). The mixture was stirred with heating to reflux, applying a jacket temperature of 140-150° C. for 84 hours. The mixture was cooled to 86-90° C. and filtered through a bed of filter aid. The reactor was rinsed with hot (86-90° C.) toluene (120 L), and the hot toluene was then used to wash the bed of filter aid. The rinse of the reactor and the following wash of the bed of filter aid was repeated two times with hot toluene (120 L), and once with hot (70° C.) ethyl acetate (60 L). All the toluene and ethyl acetate filtrates were combined and cooled to 2-6° C. over approximately 6 hours. The mixture was stirred at 2-6° C. for approximately half an hour.

Unconverted starting material was collected by filtration, and dried in vacuo at 43-47° C. Yield 32.0 kg.

The filtrate from the isolation of unconverted starting material was cooled to 10-16° C. with stirring, and a mixture of sodium hydroxide (26.40 kg) and water (162.0 L) was added at 10-16° C. The reaction mixture was then stirred for approximately half an hour at 10-16° C., then the agitation was stopped, and the phases were allowed to settle. The lower aqueous phase was discarded, and then a mixture of sodium hydroxide (26.40 kg) and water (162 L) was added with stirring at 10-16° C. The mixture was stirred for approximately one hour, then agitation was stopped, and the phases were allowed to settle. The lower aqueous phase was discarded and the organic phase was transferred to a container. The reactor was rinsed with toluene, and then the organic phase was transferred back to the reactor through a Cartridge filter.

The solution was concentrated as much as possible in vacuo applying a temperature of ≤70° C. Ethanol (90.0 L) was added, and the mixture was heated to 47-53° C., and stirred at that temperature for 10-15 minutes. Then the mixture was concentrated as much as possible in vacuo at a temperature ≤55° C. Ethanol (120.0 L) was added to the reactor, the mixture was heated to reflux with stirring, and water (90.0 L) was added with heating, keeping the mixture at reflux. The mixture was cooled to 2-8° C. over approximately 10 hours and stirred at that temperature for approximately half an hour.

The product was isolated by filtration, washed with a mixture of ethanol (30.0 L) and water (22.8 L), and dried in vacuo at 43-47° C. Yield 21.80 kg (24% but 51% if corrected for recovered starting material). $^1$H NMR (600 MHz, DMSO-d6) δ 7.30 (d, J=9.0 Hz, 1H), 6.75 (d, J=9.0 Hz, 1H), 3.88 (s, 3H), 2.91-2.84 (m, 2H), 2.84-2.77 (m, 2H), 2.49 (s, 3H), 2.30-2.22 (m, 2H), 2.22-2.12 (m, 2H).

Step (1) was repeated as necessary in order to produce the needed amount of 1-(7-methoxyspiro[1,3-benzodioxole-2,4'-tetrahydrothiopyran]-4-yl)ethanone.

Step (2a): Preparation of 1-(7-hydroxyspiro[1,3-benzodioxole-2,4'-tetrahydro-thiopyran]-4-yl)ethanone A reactor was charged with 1-(7-methoxyspiro[1,3-benzodioxole-2,4'-tetrahydro-thiopyran]-4-yl)ethanone (26.0 kg, 92.7 mol), potassium carbonate (14 kg, 101 mol), dimethylformamide (104 L), and 5-tert-butyl-2-methyl-benzenethiol (26.8 kg, 149 mol). The mixture was heated with stirring to 85-92° C. until a conversion of ≥98% was achieved, as indicated by HPLC. The mixture was then cooled to 25° C., added water (104 L) and sodium hydroxide (28% in water, 21.4 kg), and stirred for ≥10 minutes. If pH of the mixture was below 12, more sodium hydroxide (28% in water) was added. Then toluene (65 L) was added, and stirring was continued for ≥15 minutes. The agitation was stopped, and the phases were allowed to settle. The phases were separated and the organic phase was discarded. The two lower aqueous phases were stirred with toluene (65 L) and the mixture was stirred for ≥15 minutes. The agitation was stopped, allowing the phases to settle. The phases were separated and the organic phase was discarded. The two aqueous phases were returned to the reactor and hydrochloric acid (18% in water, 67.6 kg) was added slowly with stirring in order to control the gas evolution. The resulting mixture was stirred for ≥10 minutes. More hydrochloric acid (18% in water, 10.2 kg) was added in order to achieve pH≤6.

The temperature of the mixture was adjusted to 35-45° C. and kept there during the following extractions. Ethyl acetate (156 L) was added and the mixture was stirred for ≥30 minutes. The stirring was stopped, and the phases were allowed to settle. The phases were separated. The aqueous phase was stirred with ethyl acetate (78 L) for ≥30 minutes. The agitation was stopped, and the phases were allowed to settle. The aqueous phases was discarded. The two ethyl acetate phases were combined in the reactor and stirred with water (78 L) for ≥15 minutes. The stirring was stopped, and the phases were allowed to separate. The aqueous phase was discarded.

The organic phases were concentrated as much as possible with a jacket temperature of 50-60° C. and applying a vacuum. Then heptane (39 L) was added, and the resulting mixture was cooled to ≤5° C. with a rate of ≤10° C./h, and kept at that temperature for ≥3 hours. The title compound was isolated by filtration, washed with a cold (≤5° C.) mixture of ethyl acetate (10 L) and heptane (10 L), and dried in vacuo at 40-50° C. Yield 19.75 kg (80%). $^1$H NMR (600 MHz, DMSO-d6) δ 10.51 (s, 1H), 7.18 (d, J=9.0 Hz, 1H), 6.50 (d, J=9.0 Hz, 1H), 2.93-2.85 (m, 2H), 2.84-2.78 (m, 2H), 2.46 (s, 3H), 2.31-2.23 (m, 2H), 2.20-2.11 (m, 2H).

Step (2b): Tetrabutylammonium 7-acetylspiro[1,3-benzodioxole-2,4'-tetrahydro-thiopyran]-4-olate 1-(7-hydroxyspiro[1,3-benzodioxole-2,4'-tetrahydrothiopyran]-4-yl)ethanone (19.75 kg, 74.16 mol) was charged to a suitable reactor followed by tetrabutylammonium hydroxide (40% solution in water, 53.0 kg, 81.7 mol). The jacket temperature was set to 60° C. and the mixture was stirred until all had dissolved. A saturated solution of sodium chloride in water (59.2 kg) was added and stirring was continued with a jacket temperature of 60° C. for ≥20 minutes. The agitation was stopped, allowing the phases to separate. The lower aqueous phase was discarded. The mixture in the reactor was stirred again with a jacket temperature of 60° C. A saturated solution of sodium chloride in water (29.6 kg) and then water (25 L) were added. The mixture was stirred for ≥15 minutes at a temperature ≥35° C. in the mixture. The mixture was cooled to 0-5° C. at a rate of approximately 20° C./hr, the mixture was seeded at 40° C. and again at 35° C. The mixture was stirred at 0-5° C. for ≥2 hours, and then the title compound was isolated by filtration and dried in vacuo at 40-50° C. Yield 32.9 kg (87%). $^1$H NMR (600 MHz, DMSO-d6) δ 6.94 (d, J=9.1 Hz, 1H), 5.74 (d, J=9.1 Hz, 1H), 3.23-3.07 (m, 8H), 2.87-2.72 (m, 4H), 2.25 (s, 3H), 2.16-2.07 (m, 2H), 2.06-1.96 (m, 2H), 1.62-1.51 (m, 8H), 1.30 (h, J=7.4 Hz, 8H), 0.93 (t, J=7.4 Hz, 12H).

Step (3): 1-[7-(difluoromethoxy)spiro[1,3-benzodioxole-2,4'-tetrahydrothiopyran]-4-yl]ethanone Tetrabutylammonium 7-acetylspiro[1,3-benzodioxole-2,4'-tetrahydrothiopyran]-4-olate (32.93 kg, 64.85 mol) and dimethylformamide (198 L) were added to a reactor.

The mixture was stirred until all had dissolved. Chlorodifluoromethane (39.5 kg, 457 mol) was added to the solution via a dip pipe on the reactor. The reaction mixture was heated to 50-55° C. and stirred until ≤4% of the starting material was left as indicated by HPLC. The reaction mixture was cooled to 20-25° C. and transferred to a container via a filter. The reactor and the solid in the filter was washed with dimethylformamide (10 L) which was added to the container as well.

Water (198 L) and sodium hydroxide (28% in water, 11.0 kg) were charged to the reactor and heated to 45-55° C. The reaction mixture in the container was added slowly to the reactor with stirring, keeping the temperature at 45-55° C. The mixture was then cooled to 5-10° C. and stirred at that temperature for ≥2 hours. The product was isolated by filtration, washed with water (82 L), and dried in vacuo at 45-55° C. with a bleed of nitrogen. Yield 19.08 kg (94%). $^1$H NMR (600 MHz, DMSO-d6) δ 7.34 (t, J=73.1 Hz, 1H), 7.32 (d, J=9.1 Hz, 1H), 6.86 (d, J=9.1 Hz, 1H), 2.92-2.80 (m, 4H), 2.54 (s, 3H), 2.34-2.27 (m, 2H), 2.27-2.19 (m, 2H).

Step (4) 2-(3,5-dichloro-4-pyridyl)-1-[7-(difluoromethoxy)spiro[1,3-benzodioxole-2,4'-tetrahydrothiopyran]-4-yl]ethanone Dimethyl formamide (96 L) was charged to a suitable reactor followed by addition of potassium tert-butoxide (17.60 kg, 156.8 mol). Transfer of potassium tert-butoxide was ensured with a rinse of dimethyl formamide (3 L), and the mixture was stirred until potassium tert-butoxide had dissolved. The solution was transferred from the reactor to a container, the reactor was rinsed with dimethyl formamide (6 L), which was transferred to the container as well.

The reactor was charged with 1-[7-(difluoromethoxy)spiro[1,3-benzodioxole-2,4'-tetrahydrothiopyran]-4-yl]ethanone (19.08 kg, 60.32 mol), 3,4,5-trichloropyridine (14.30 kg, 78.38 mol), and dimethylformamide (96 L). The mixture was stirred and cooled to 10-15° C., and then the solution of potassium tert-butoxide in dimethyl-formamide was added slowly, keeping the temperature of the reaction mixture at 5-25° C. The transfer of the potassium tert-butoxide solution was ensured with a rinse of dimethyl formamide (6 L). The mixture was heated to 20-25° C. and stirred until the conversion was ≥90% as indicated by HPLC. Content of the impurity of formula (XII) in the reaction mixture: 12%

Water (96 L) was added slowly with cooling to the reaction mixture keeping the temperature between 20-30° C. This was followed by the addition of saturated sodium chloride in water (115.2 kg) and ethyl acetate (134 L). The mixture was stirred for 20-60 minutes and then the agitation was stopped, allowing the phases to settle. The phases were separated, and the aqueous phase was returned to the reactor. Ethyl acetate (96 L) was added, and the mixture was stirred for 20-60 minutes. The agitation was stopped, allowing the phases to settle. The phases were separated. The organic phases were combined in the reactor and stirred with water (48 L) and saturated sodium chloride in water (57.8 kg) for ≥20 minutes. The agitation was stopped allowing the phases to settle. The lower aqueous phase was discarded, and water (48 L) and saturated sodium chloride (57.6 kg) were added. The mixture was agitated for 20-60 minutes, and then the agitation was stopped, allowing the phases to settle. The lower aqueous phase was discarded, and water (84 L) and sodium hydroxide (28% in water, 14.0 kg) were added. The mixture was stirred for 20-60 minutes and then the agitation was stopped, allowing the phases to settle. The lower aqueous phase was discarded.

The organic phase in the reactor was concentrated by use of vacuum and heating with a jacket temperature of 50-65° C. to a residual volume of approximately 40 L. Ethanol (57 L) was charged to the reactor, and the mixture was heated to reflux until a clear solution was obtained. The mixture was cooled to 5° C. over ≥5 hours and stirred at that temperature for ≥3 hours. The product was isolated by filtration, transfer was ensured with a rinse of ethanol (10 L). The product was washed with cold (≤5°) ethanol (48 L) and dried in vacuo at 45-55° C. Yield 15.57 kg (56%). $^1$H NMR (600 MHz, Chloroform-d) δ 8.52 (s, 2H), 7.46 (d, J=8.9 Hz, 1H), 6.80 (d, J=8.9 Hz, 1H), 6.73 (t, J=73.3 Hz, 1H), 4.59 (s, 2H), 3.01-2.85 (m, 4H), 2.47-2.30 (m, 4H). HPLC: Purity: 97.8%, content of the impurity of the formula (XII): 1.0%.

Step (5): 2-(3,5-dichloro-1-oxido-pyridin-1-ium-4-yl)-1-[7-(difluoromethoxy)-1',1'-dioxo-spiro[1,3-benzodioxole-2,4'-thiane]-4-yl]ethanone A reactor was charged with 2-(3,5-dichloro-4-pyridyl)-1-[7-(difluoromethoxy)-spiro[1,3-benzodioxole-2,4'-tetrahydrothiopyran]-4-yl]ethanone (15.6 kg, 33.7 mol) and glacial acetic acid (78.0 kg) and the mixture was cooled to 13-20° C. Per acetic acid (36-40% in acetic acid, 6.52 kg, 32.6 mol) was added slowly keeping the temperature below 40° C. The mixture was heated to 40-50° C. and stirred for 10-25 minutes. The mixture was cooled to 13-20° C. and a second portion of per acetic acid (36-40% in acetic acid, 6.51 kg, 32.5 mol) was added slowly keeping the temperature below 40° C. The mixture was heated to 40-50° C. and stirred for 10-25 minutes. The mixture was cooled to 20-30° C. and a third portion of per acetic acid (36-40% in acetic acid, 14.3 kg, 71.5 mol) was added slowly. The mixture was heated to 48-55° C. and stirred until the conversion was ≥98.5%. The mixture was cooled to 20-25° C. and a mixture of sodium metabisulphite (7.21 kg, 37.9 mol) and water (46 L) was added slowly keeping the temperature below 35° C.

2-propanol (78 L) was added and the mixture was heated to 60-65° C. and filtered hot. The reactor was cleaned and the filtrated reaction mixture was returned to the reactor. The mixture was heated to 60-65° C. and water (234 L) was added slowly keeping the temperature above 55° C. The mixture was stirred for 30-60 minutes at 60-65° C., cooled slowly to 5° C. over 12 hours, and stirred at 0-10° C. for ≥2 hours. The raw product was isolated by filtration, washed with water (27 L), and dried in vacuo for approximately two hours.

The solid was returned to the reactor and heated to reflux with ethanol (390 L). The mixture was then cooled to 68-72° C. and seeded. The mixture was cooled to 5° C. over 13 hours and stirred at 0-10° C. for ≥2 hours. The product was isolated by filtration, washed with a cold (0-10° C.) mixture of water (4 L) and ethanol (39 l), and dried in vacuo at 45-55° C. with a bleed of nitrogen. Yield 14.6 kg (85%). 1H NMR (600 MHz, Chloroform-d) δ8.23 (s, 2H), 7.52 (d, J=9.1 Hz, 1H), 6.90 (d, J=9.1 Hz, 1H), 6.71 (t, J=72.3 Hz, 1H), 4.49 (s, 2H), 3.47-3.38 (m, 2H), 3.33-3.24 (m, 2H), 2.83-2.75 (m, 2H), 2.75-2.68 (m 2H). HPLC: purity 98.6%.

Example 2

1-(7-hydroxyspiro[1,3-benzodioxole-2,4'-tetrahydrothiopyran]-4-yl)ethanone

Sodium methoxide in methanol (30%, 64.2 mL, 0.34 mol) was added to a solution of 1-(7-methoxyspiro[1,3-benzodioxole-2,4'-tetrahydrothiopyran]-4-yl)ethanone (50.0 g, 0.178 mol) in dimethylformamide (250 mL) at 25-30° C. Then 1-dodecane-thiol (64.88 mL, 0.271 mol) was added at 25-30° C. and the mixture was heated to 95-100° C. for three hours. The reaction mixture was cooled to 25-30° C. and sodium hydroxide (28% in water, 50 mL) and water (250 mL) were added. The resulting mixture was stirred for half an hour and then the mixture was extracted with toluene (250 mL) three times. The aqueous solution was acidified with hydrochloric acid (6M) to approximately pH 6 and extracted with ethyl acetate (250 mL) four times. The ethyl acetate extracts were combined, washed with brine (250 mL) four times, and concentrated to approximately 50 mL using a rotary evaporator. Heptane (300 mL) was added and the mixture was stirred for one hour at ambient temperature. The product was isolated by filtration, washed with heptane (100 mL), and dried. Yield 44.3 g (93%). NMR complied with NMR of the product from step (2a) in Example 1.

Example 3

1-[7-(difluoromethoxy)spiro[1,3-benzodioxole-2,4'-tetrahydrothiopyran]-4-yl]-ethanone A mixture of 1-(7-hydroxyspiro[1,3-benzodioxole-2,4'-tetrahydrothiopyran]-4-yl)ethanone (221.6 g, 0.8322 mol), potassium carbonate (161.3 g, 1.167 mol), sodium chlorodifluoroacetate (292.0 g, 1.915 mol), dimethylformamide (1.50 L), and water (500 mL) was stirred in a 5 liter reaction flask and heated slowly to 106-111° C., gas evolution was observed from approximately 78° C. The reaction mixture was stirred at 106-111° C. until the gas evolution had ceased, approximately two hours. The mixture was cooled with an ice-water bath, and water (1.00 L) was added slowly at 30-32° C. The resulting suspension was cooled further to 6° C. under stirring. The raw product was isolated by filtration and washed with water.

The wet raw product was stirred with ethyl acetate (1.66 L) and sodium hydroxide (1 M, 560 mL) for approximately 20 minutes, and then the phases was separated in a separatory funnel. The lower aqueous phase was discarded and the organic phase was washed twice with water (two times 560 mL). The organic phase was concentrated using a rotary evaporator (in vacuo with 60° C. in the water bath) to approximately 450 mL. Ethyl acetate (1.56 L) was added, and the mixture was concentrated again using a rotary evaporator as above to approximately 450 mL. Ethyl acetate (1.44 L) was added, and the unclear solution was filtered, transferring and washing with a fresh portion of ethyl acetate (100 mL). The combined filtrates were filtered through a plug of activated carbon (6.0 g), transferring and washing with ethyl acetate (200 mL). The combined filtrates were concentrated on a rotary evaporator as above to approximately 450 mL. The resulting hot solution (approximately 60° C.) was stirred at ambient temperature while heptane (2.00 L) was added slowly over approximately half an hour. The suspension was stirred at ambient temperature for 14 hours.

The mixture was stirred in an ice-water bath for approximately 2.5 hours, the temperature of the mixture was then 4° C. The product was isolated by filtration, washed with an ice-cold mixture of heptane and ethyl acetate (10:1, 200 mL), and dried in vacuo at 50° C. with a bleed of air. Yield 201 g (76%). NMR complied with NMR of the product from step 3 in example 1.

Example 4

1-[7-(difluoromethoxy)spiro[1,3-benzodioxole-2,4'-tetrahydrothiopyran]-4-yl]-ethanone Sodium hydroxide (6.16 g, 154 mmol) was dissolved in water (40 mL) and the solution was stirred with cooling in an ice-water bath. 1-(7-hydroxyspiro[1,3-benzodioxole-2,4'-tetrahydrothiopyran]-4-yl)ethanone (2.00 g, 7.51 mmol) and acetonitril (20 mL) were added, and stirring with cooling was continued. Diethyl bromodifluoromethylphosphonate (2.67 mL, 15.0 mmol) was added in one portion at 6° C., and stirring with cooling was continued for approximately 20 minutes. The cooling bath was removed, and the mixture was stirred for approximately 21 hours at ambient temperature.

The phases were separated using a separatory funnel, and the water phase was extracted with ethyl acetate (20 mL). The combined organic phases were washed with water (20 mL) and then with brine (20 mL). The organic phase was concentrated to dryness using a rotary evaporator as in example 3. Ethyl acetate (20 mL) was added to the residue, and the mixture was concentrated to dryness once again using the rotary evaporator.

The residue was dissolved in ethyl acetate (30 mL) and filtered, transferring and washing with ethyl acetate (20 mL). The combined filtrates was concentrated to dryness using a rotary evaporator as above, giving the title compound as a yellowish solid. Yield 2.14 g (90%). NMR complied with NMR of the product from step 3 in example 1.

Example 5

1-[7-(difluoromethoxy)spiro[1,3-benzodioxole-2,4'-tetrahydrothiopyran]-4-yl]-ethanone Sodium hydroxide (301 g, 7.52 mol) was stirred with water (2.0 L), and the resulting solution was cooled with an ice-water bath. 1-(7-hydroxyspiro[1,3-benzodioxole-2,4'-tetrahydrothiopyran]-4-yl)ethanone (100.1 g, 0.3757 mol) and acetonitrile (1.0 L) were added. Diethyl bromodifluorophosphonate (150.5 g, 0.5637 mol) was added slowly over approximately 40 minutes at a temperature of 15-20° C. in the reaction mixture. Stirring was continued for another approximately two hours at 15-20° C. The phases were separated.

Water (920 mL) was added slowly to the organic phase with stirring and the resulting suspension was stirred at ambient temperature for approximately 18 hours. The product was isolated by filtration, washed with a 1:1 mixture of acetonitrile and water (120 mL), and dried in vacuo at 50° C. with a bleed of air. Yield 108 g (91%). NMR complied with NMR of the product from step 3 in example 1.

CLAUSES

In view of the description the present inventors have in particular provided:

Clause 0. A method for the preparation of a compound of formula (I)

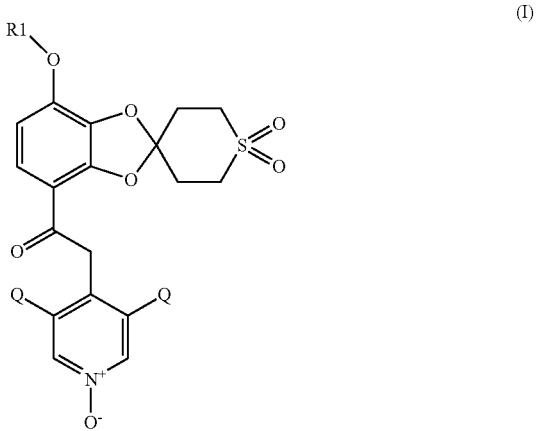

wherein $R_1$ is selected from $CHF_2$ and $CF_3$, Q is selected from chloro, bromo and fluoro, comprising one or more of the following steps:
(1) reacting a compound of formula (II)

wherein $R_2$ is selected from hydrogen, $C_{1-6}$-alkyl and arylalkyl, $R_{21}$ is selected from hydrogen and $C(O)R_{22}$, and $R_{22}$ is selected from hydrogen and $C_{1-6}$-alkyl; with a compound of formula (III)

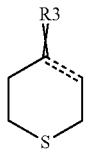
(III)

wherein " ⨯ " represents a single bond, a double bond or two single bonds, and when "•" represents a double bond or two single bonds, "═══" is a single bond, and when " ⨯ " represents a single bond, "═══" is a double bond; $R_3$ represents oxygen when " ⨯ " represents a double bond and $R_3$ represents O—$C_{1-6}$-alkyl when " ⨯ " represents a single bond or two single bonds; in the presence of an acid catalyst to form a compound of formula (IV)

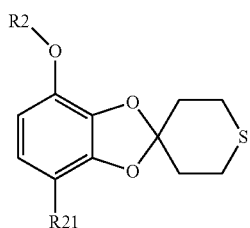
(IV)

wherein $R_2$ and $R_{21}$ is as defined above;

(2a) reacting the resulting compound of formula (IV) with an aromatic or aliphatic thiol, to form a compound of formula (VI)

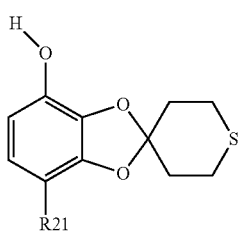
(VI)

wherein $R_{21}$ is defined above;

(2b) reacting the compound of formula (VI) with aqueous $N(Bu)_4{}^+OH^-$ to form a compound of formula (VII)

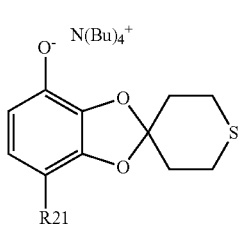
(VII)

wherein $R_{21}$ is as defined above;

(3) alkylating the resulting compound of formula (VII) with a hydrochlorofluorocarbon reagent,

$R_1$—Cl (VIII)

wherein $R_1$ is as defined above, to form a compound of formula (IX)

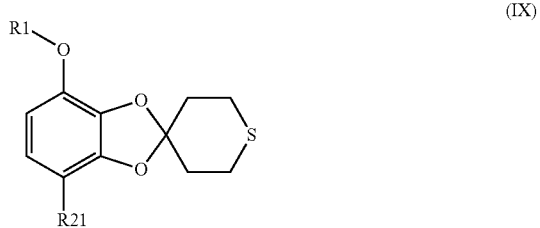
(IX)

wherein $R_1$ and $R_{21}$ are as defined above;

(4) reacting the compound of formula (IX) with a pyridine compound of formula (X)

(X)

wherein Q is as defined above and $Q_x$ is selected from chloro, bromo, fluoro and iodo to form a compound of formula (XI);

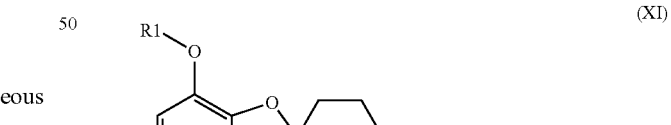
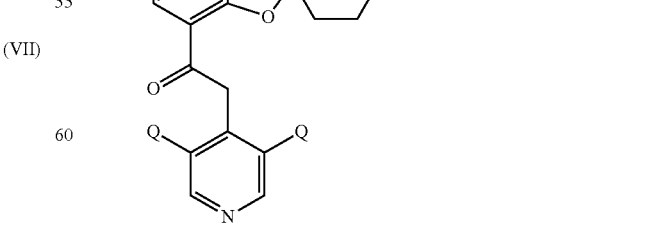
(XI)

wherein $R_1$ and Q are as defined above; and (5) oxidating the resulting compound of formula (XI) to prepare the compound of formula (I)

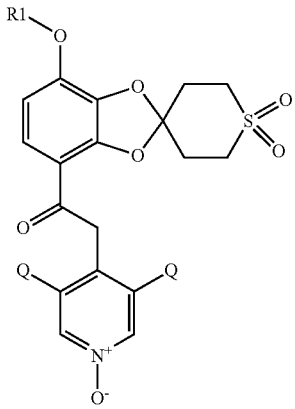
(I)

wherein $R_1$ and Q are as defined above.

Clause 1. A method for the preparation of a compound of formula (I)

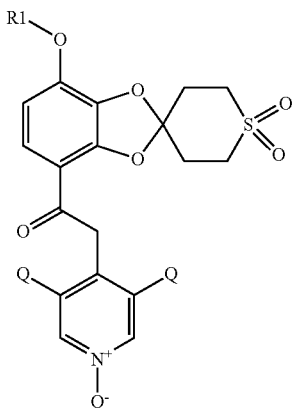
(I)

wherein $R_1$ is selected from $CHF_2$ and $CF_3$, Q is selected from chloro, bromo and fluoro, comprising each of the following steps:

(1) reacting a compound of formula (II)

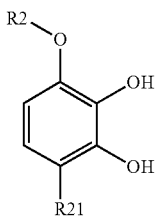
(II)

wherein $R_2$ is selected from hydrogen, $C_{1-6}$-alkyl and arylalkyl, $R_{21}$ is selected from hydrogen and $C(O)R_{22}$, and $R_{22}$ is selected from hydrogen and $C_{1-6}$-alkyl; with a compound of formula (III)

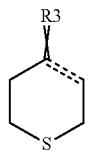
(III)

wherein " ⋈ " represents a single bond, a double bond or two single bonds, and when " ⋈ " represents a double bond or two single bonds, "═" is a single bond, and when " ⋈ " represents a single bond, "═" is a double bond; $R_3$ represents oxygen when " ⋈ " represents a double bond and $R_3$ represents $O-C_{1-6}$-alkyl when " ⋈ " represents a single bond or two single bonds; in the presence of an acid catalyst to form a compound of formula (IV)

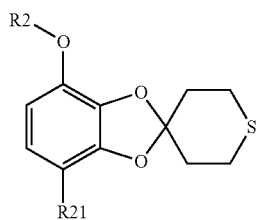
(IV)

wherein $R_2$ and $R_{21}$ is as defined above;

(2a) reacting the resulting compound of formula (IV) with an aromatic or aliphatic thiol, to form a compound of formula (VI)

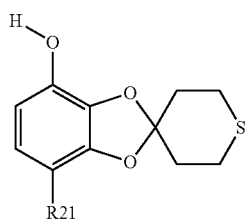
(VI)

wherein $R_{21}$ is defined above;

(2b) reacting the compound of formula (VI) with aqueous $N(Bu)_4^+OH^-$ to form a compound of formula (VII)

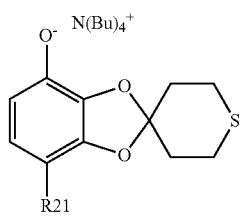
(VII)

wherein $R_{21}$ is as defined above;

(3) alkylating the resulting compound of formula (VII) with a hydrochlorofluorocarbon reagent, $$R_1-Cl \quad (VIII)$$

wherein R₁ is as defined above, to form a compound of formula (IX)

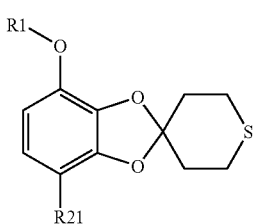

wherein R₁ and R₂₁ are as defined above;
(4) reacting the compound of formula (IX) with a pyridine compound of formula (X)

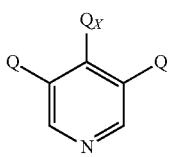

wherein Q is as defined above and $Q_x$ is selected from chloro, bromo, fluoro and iodo to form a compound of formula (XI);

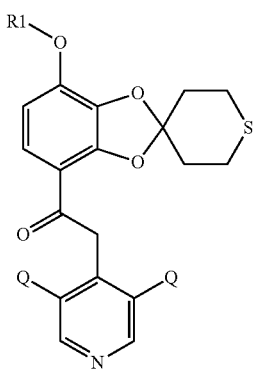

wherein R₁ and Q are as defined above; and
(5) oxidating the resulting compound of formula (XI) to prepare the compound of formula (I)

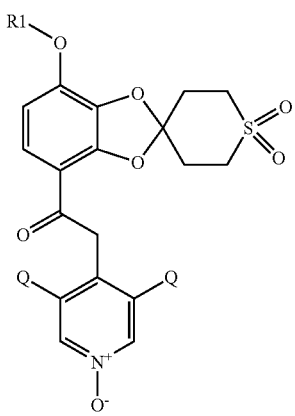

wherein R₁ and Q are as defined above.

Clause 2. The method according to clause 1 wherein the deprotection in step (2a) is conducted in a solvent e.g. selected from NMP, DMSO, DMF, methanol, ethanol and mixtures hereof, in the presence of a base, e.g. selected from $K_2CO_3$, $Na_2CO_3$, $KHCO_3$, $NaHCO_3$, $CsCO_3$, TEA and DIPEA, potassium tert-butoxide, lithium tert-butoxide, sodium methoxide, sodium ethoxide.

Clause 3. The method according to clause 2 wherein the solvent is DMF and the base is $K_2CO_3$.

Clause 4. The method according to clause 2 where the solvent is a mixture of DMF and methanol and the base is sodium methoxide.

Clause 5. The method according to any one of the preceding clauses wherein the reaction in step (3) is conducted using a hydrochlorofluorocarbon R₁—Cl compound in the presence of a polar solvent, e.g. selected from DMF, NMP, DMI, DMSO, EtOAc and THF.

Clause 6. The method according to clause 5 wherein the reaction is conducted using chlorodifluoromethane in DMF.

Clause 7. The method according to any one of the preceding clauses wherein in step (4) the coupling is conducted in a polar solvent, e.g. selected from NMP, DMF, DMI, DMSO, MeCN and THF, and mixtures hereof, in the presence of a base, e.g. selected from tert-BuOK, tert-BuOLi, tert-BuONa, sodium or potassium methoxide, sodium or potassium ethoxide, $K_2CO_3$, $Na_2CO_3$, $KHCO_3$, $NaHCO_3$, $Et_3N$ and DIPEA.

Clause 8. The method according to clause 7 wherein the polar solvent is DMF, and the base is tert-BuOK.

Clause 9. The method according to any one of the preceding clauses wherein R₁ is $CHF_2$.

Clause 10. The method according to any one of the preceding clauses wherein all of Q and $Q_x$ are chloro.

Clause 11. The method according to any one of the preceding clauses wherein the impurity of formula (XII)

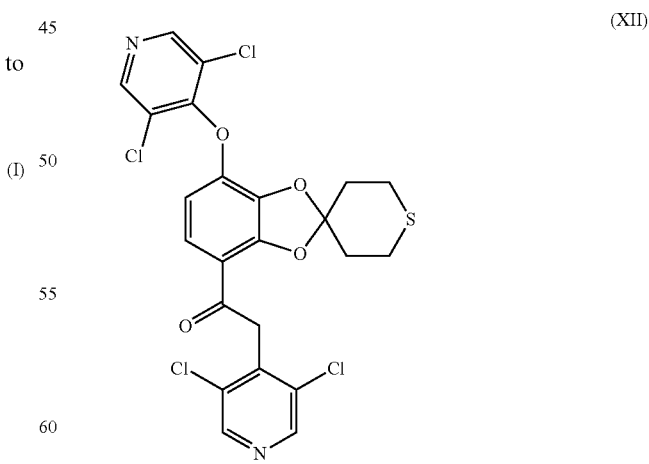

is purged from the product obtained in step (4) by crystallising said product from a solvent selected from e.g. dimethylformamide (DMF), ethanol, methanol, ethyl acetate, hexane, heptane, and mixtures thereof.

Clause 12. The method according to clause 11, wherein the solvent is a mixture of ethyl acetate and ethanol.

Clause 13. An intermediate compound of formula (VI)

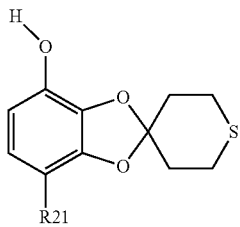

(VI)

wherein $R_{21}$ is selected from hydrogen and $C(O)R_{22}$, and $R_{22}$ is selected from hydrogen and $C_{1-6}$-alkyl.

Clause 14. The intermediate compound according to clause 13 which is 1-(7-hydroxy-spiro[1,3-benzodioxole-2,4'-tetrahydrothiopyran]-4-yl)ethanone.

Clause 15. An intermediate compound of formula (VII)

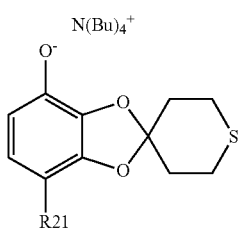

(VII)

wherein $R_{21}$ is selected from hydrogen and $C(O)R_{22}$, and $R_{22}$ is selected from hydrogen and $C_{1-6}$-alkyl.

Clause 16. The intermediate compound according to clause 15 which is tetrabutylammonium 7-acetylspiro[1,3-benzodioxole-2,4'-tetrahydrothiopyran]-4-olate.

Clause 17. An intermediate compound of formula (IX)

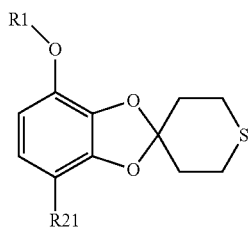

(IX)

wherein $R_1$ is selected from $CHF_2$ and $CF_3$, and $R_{21}$ is selected from hydrogen and $C(O)R_{22}$, and $R_{22}$ is selected from hydrogen and $C_{1-6}$-alkyl.

Clause 18. The intermediate compound according to clause 17 which is 1-[7-(difluoromethoxy)spiro[1,3-benzodioxole-2,4'-tetrahydrothiopyran]-4-yl]ethanone.

Clause 19. A method for preparing a compound of formula (VI)

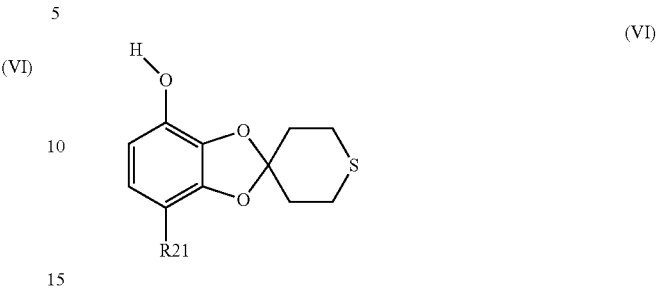

(VI)

wherein $R_{21}$ is selected from hydrogen and $C(O)R_{22}$, and $R_{22}$ is selected from hydrogen and $C_{1-6}$-alkyl, comprising reacting the compound of formula (IV) with an aliphatic or aromatic thiol.

Clause 20. The method according to clause 19, wherein the thiol is 1-dodecane-thiol.

Clause 21. The method according to clause 19, wherein the thiol is 5-tert-butyl-2-methyl-benzenethiol Clause 22. A method for preparing a compound of formula (VII)

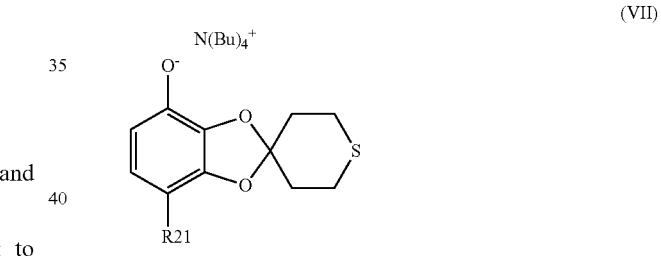

(VII)

wherein $R_{21}$ is selected from hydrogen and $C(O)R_{22}$ and $R_{22}$ is selected from hydrogen and $C_{1-6}$-alkyl, comprising step (1), (2a) and (2b) as defined in clause 1.

Clause 23. A method for preparing a compound of formula (VII)

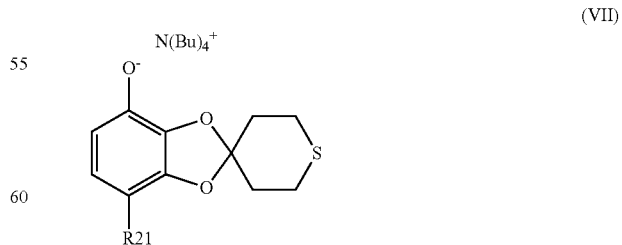

(VII)

wherein $R_{21}$ is selected from hydrogen and $C(O)R_{22}$ and $R_{22}$ is selected from hydrogen and $C_{1-6}$-alkyl, comprising step (2a) and (2b) as defined in clause 1.

Clause 24. A method for preparing a compound of formula (VII)

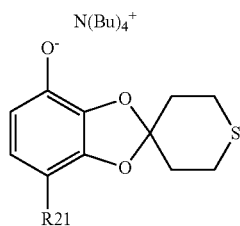

(VII)

wherein $R_{21}$ is selected from hydrogen and $C(O)R_{22}$; and $R_{22}$ is selected from hydrogen and $C_{1-6}$-alkyl, comprising step (2b) as defined in clause 1.

Clause 25. A method for preparing a compound of formula (IX)

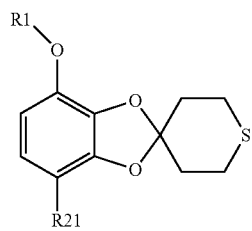

(IX)

wherein $R_1$ is selected from $CHF_2$ and $CF_3$, and $R_{21}$ is selected from hydrogen and $C(O)R_{22}$, and $R_{22}$ is selected from hydrogen and $C_{1-6}$-alkyl; comprising step (2b) and (3) as defined in clause 1.

Clause 26. A method for preparing a compound of formula (IX)

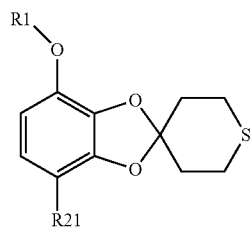

(IX)

wherein $R_1$ is selected from $CHF_2$ and $CF_3$, and $R_{21}$ is selected hydrogen and $C(O)R_{22}$, and $R_{22}$ is selected from hydrogen and $C_{1-6}$-alkyl; comprising step (3) as defined in clause 1.

Clause 27. A method for preparing a compound of formula (IX)

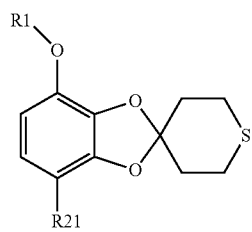

(IX)

wherein $R_1$ is selected from $CHF_2$ and $CF_3$, and $R_{21}$ is selected from hydrogen and $C(O)R_{22}$, and $R_{22}$ is selected from hydrogen and $C_{1-6}$-alkyl; comprising reacting the compound of formula (VI) with a difluorocarbene source in a polar solvent in the presence of a base.

Clause 28. The method according to clause 27, wherein the difluorocarbene source is sodium chlorodifluoroacetate.

Clause 29. The method according to clause 27, wherein the difluorocarbene source is diethyl bromodifluoromethylphosphonate.

Clause 30. The method according to clause 28, wherein the polar solvent is a mixture of water and DMF.

Clause 31. The method according to clause 29, wherein the polar solvent is a mixture of water and acetonitrile.

Clause 32. The method according to clause 30, wherein the base is $K_2CO_3$.

Clause 33. The method according to clause 31, wherein the base is NaOH.

Clause 34. A method for preparing a compound of formula (I)

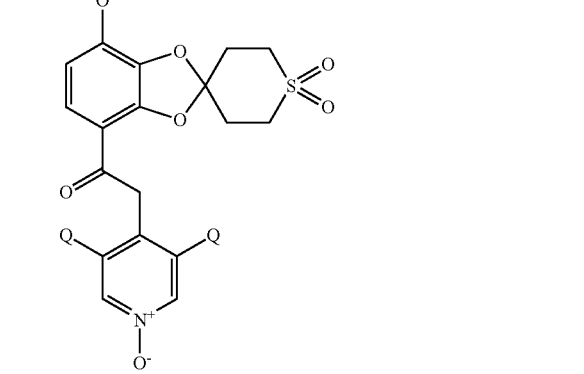

(I)

wherein $R_1$ is selected from $CHF_2$ and $CF_3$, and Q is selected from chloro, bromo and fluoro, obtained by method of clause 1.

Clause 35. A method for preparing a compound of formula (I)

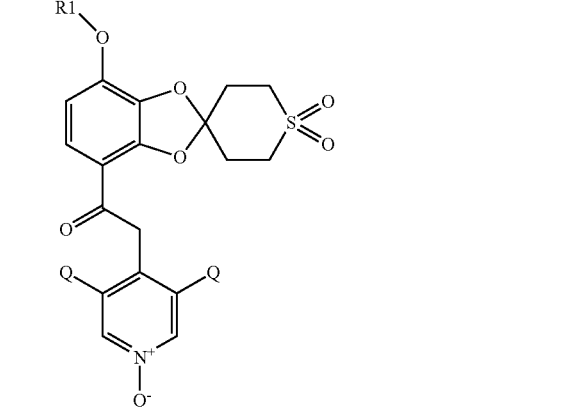

(I)

wherein $R_1$ is selected from $CHF_2$ and $CF_3$, and Q is selected from chloro, bromo and fluoro, comprising each of the steps (2a), (2b), (3) and (4) as defined in clause 1, and subsequently oxidation of the resulting compound.

Clause 36. A method for preparing a compound of formula (I)

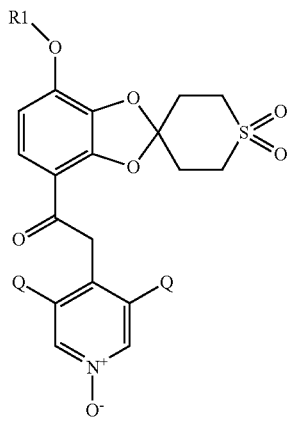

wherein R₁ is selected from CHF$_2$ and CF$_3$, and Q is selected from chloro, bromo and fluoro, comprising each of the steps (2b), (3) and (4) as defined in clause 1, and subsequently oxidation of the resulting compound.

Clause 37. A method for preparing a compound of formula (I)

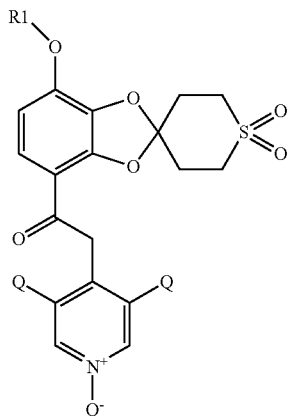

wherein R₁ is selected from CHF$_2$ and CF$_3$, and Q is selected from chloro, bromo and fluoro, comprising each of the steps (3) and (4) as defined in clause 1, and subsequently oxidation of the resulting compound.

Clause 38. A method for preparing a compound of formula (I)

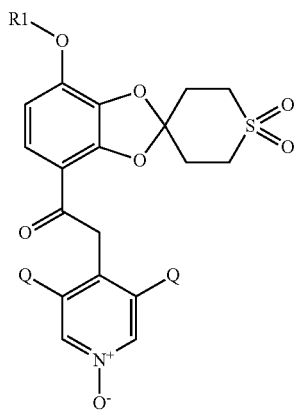

wherein R₁ is selected from CHF$_2$ and CF$_3$, and Q is selected from chloro, bromo and fluoro, comprising each of the steps: (2a), (2b+3) and (4), and subsequently oxidation of the resulting compound.

Clause 39. A compound of formula (I)

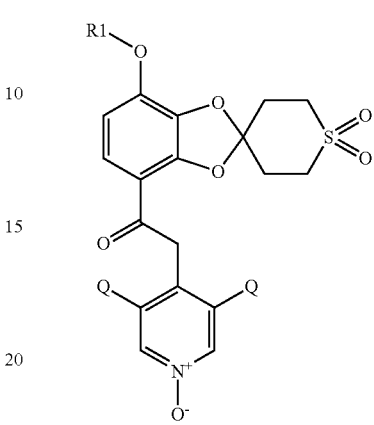

wherein R₁ is selected from CHF$_2$ and CF$_3$, and Q is selected from chloro, bromo and fluoro, obtained by method of clause 1.

Clause 40. A compound of formula (I)

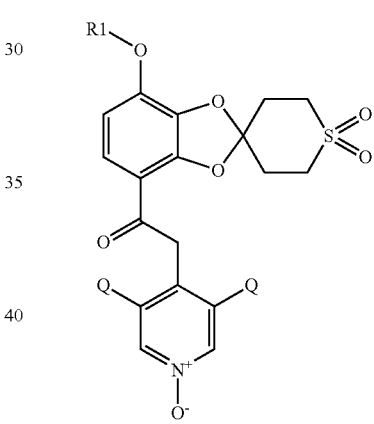

wherein R₁ is selected from CHF$_2$ and CF$_3$, and Q is selected from chloro, bromo and fluoro, made by the steps (2a), (2b), (3) and (4) as defined in clause 1, followed by oxidation of the resulting compound.

Clause 41. A compound of formula (I)

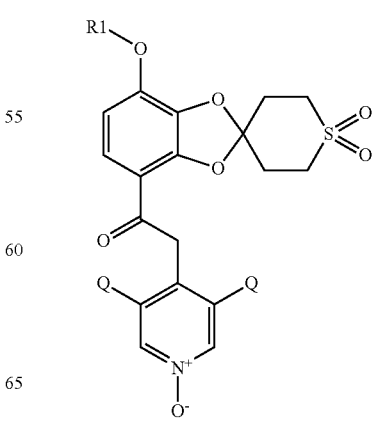

wherein R₁ is selected from CHF₂ and CF₃, and Q is selected from chloro, bromo and fluoro, made by the steps (2b), (3) and (4) as defined in clause 1, followed by oxidation of the resulting compound.

Clause 42. A compound of formula (I)

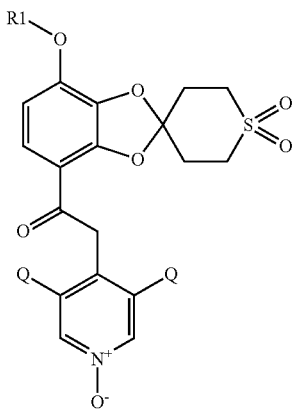

(I)

wherein R₁ is selected from CHF₂ and CF₃, and Q is selected from chloro, bromo and fluoro, made by the steps (3) and (4) as defined in clause 1, followed by oxidation of the resulting compound.

Clause 43. A compound of formula (I)

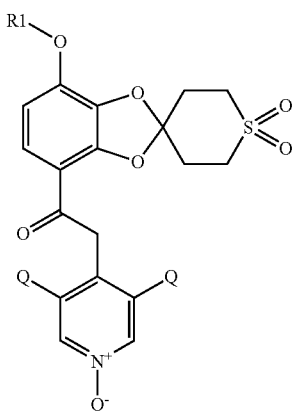

(I)

wherein R₁ is selected from CHF₂ and CF₃, and Q is selected from chloro, bromo and fluoro, made by the steps (2a), (2b+3) and (4), followed by oxidation of the resulting compound.

The invention claimed is:

1. A method for the preparation of a compound of formula (I)

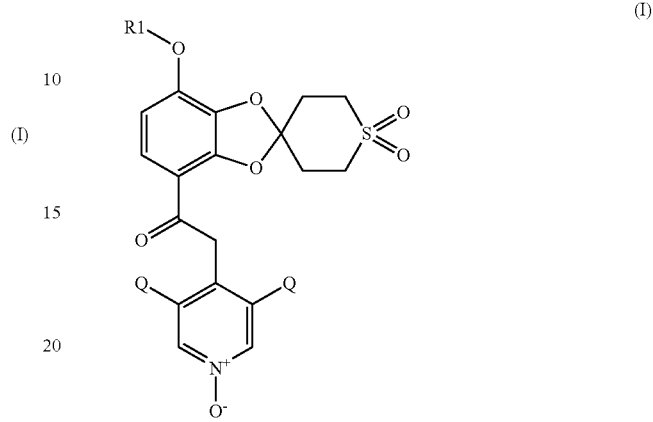

(I)

wherein R₁ is selected from CHF₂ and CF₃, and Q is selected from chloro, bromo and fluoro, the method comprising each of the following steps:

(1) reacting a compound of formula (II)

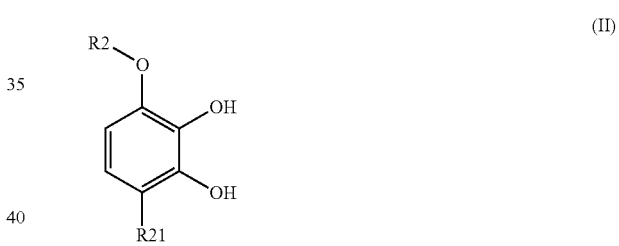

(II)

wherein R₂ is selected from $C_{1-6}$-alkyl, and arylalkyl, and R₂₁ is C(O)CH₃ with a compound of formula (III)

(III)

wherein " ~~~ " represents a single bond, a double bond, or two single bonds, and when " ~~~ " represents a double bond or two single bonds, "===" is a single bond, and when " ~~~ " represents a single bond, "===" is a double bond; R₃ represents oxygen when " ~~~ " represents a double bond and R₃ represents O—$C_{1-6}$-alkyl when " ~~~ " represents a single bond or two single bonds; in the presence of an acid catalyst to form a compound of formula (IV)

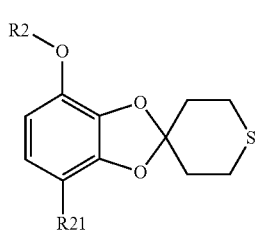

wherein R₂ and R₂₁ are as defined above;
(2a) reacting the resulting compound of formula (IV) with an aromatic or aliphatic thiol to form a compound of formula (VI)

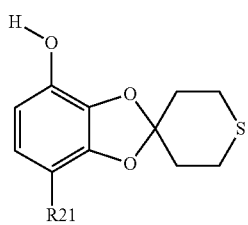

wherein R₂₁ is as defined above;
(2b) reacting the resulting compound of formula (VI) with aqueous N(Bu)₄⁺OH⁻ to form a compound of formula (VII)

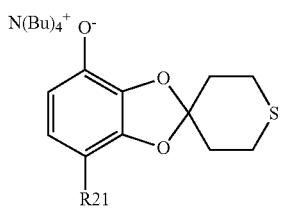

wherein R₂₁ is as defined above;
(3) alkylating the resulting compound of formula (VII) with a hydrochlorofluorocarbon reagent,

wherein R₁ is as defined above, to form a compound of formula (IX)

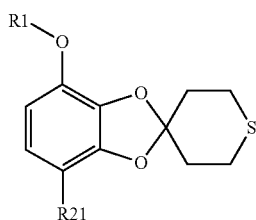

wherein R₁ and R₂₁ are as defined above;
(4) reacting the resulting compound of formula (IX) with a pyridine compound of formula (X)

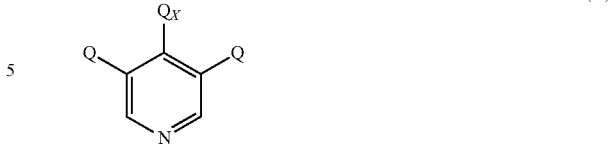

wherein Q is as defined above and Q$_x$ is selected from chloro, bromo, fluoro, and iodo to form a compound of formula (XI);

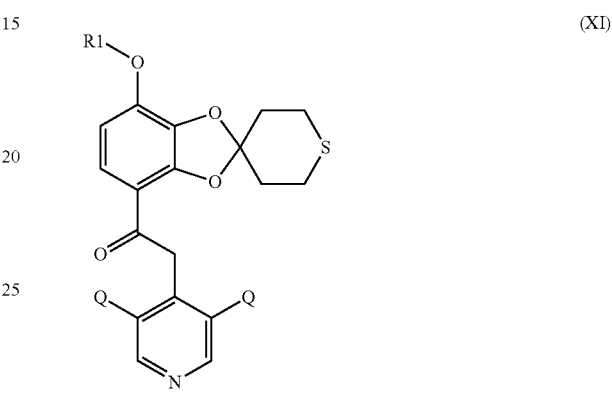

wherein R₁ and Q are as defined above; and
(5) oxidating the resulting compound of formula (XI) to prepare the compound of formula (I)

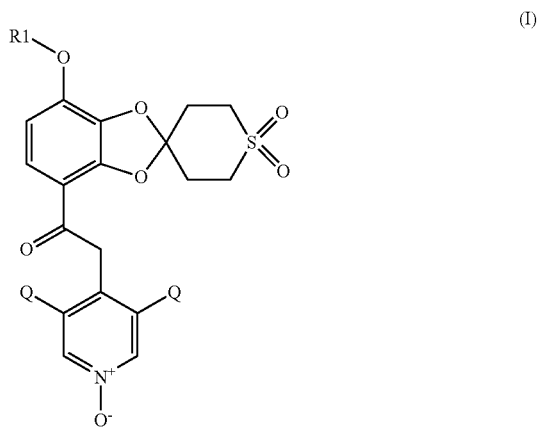

wherein R₁ and Q are as defined above.

2. The method according to claim 1 wherein the reaction in step (2a) is conducted in a solvent selected from NMP, DMSO, DMF, methanol, ethanol, and mixtures thereof, and in the presence of a base.

3. The method according to claim 1 wherein the reaction in step (3) is conducted using a hydrochlorofluorocarbon in the presence of a polar solvent.

4. The method according to claim 1 wherein the reaction in step (4) is conducted in a polar solvent, and in the presence of abase.

5. The method according to claim 1 wherein R₁ is CHF₂.

6. The method according to claim 1 wherein each Q and each Q$_x$ are chloro.

7. The method according to claim 1, wherein the method produces a compound of formula (I)

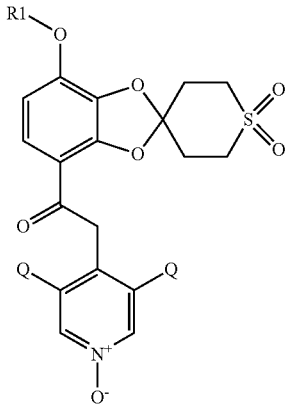
(I)

wherein $R_1$ is selected from $CHF_2$ and $CF_3$, and Q is selected from chloro, bromo, and fluoro.

8. The method according to claim 1, wherein the acid catalyst of reaction in step (1) is a silicate mineral selected from Montmorillonite K10, Montmorillonite K30, Montmorillonite KSF, Zeolite HSZ-341NHA, Zeolite HSZ-331NHA, Zeolite HSZ-350HUA, and Zeolite HSZ-360HUA.

9. The method according to claim 1, wherein the reaction in step (3) is conducted using chlorodifluoromethane in an aprotic polar solvent selected from DMF (N,N-dimethylformamide), NMP (N-methylpyrolidone), DMI (1,3-dimethyl-2-imidazolidinone), DMSO (dimethyl sulfoxide), EtOAc (ethyl acetate), MeCN (acetonitrile), and THF (tetrahydrofuran), and mixtures thereof.

10. The method according to claim 1, wherein the oxidation reaction in step (5) is conducted with a reagent selected from PAA (peracetic acid) in AcOH (acetic acid), and aqueous $H_2O_2$ in formic acid or acetic acid.

11. A method for preparing a compound of formula (I)

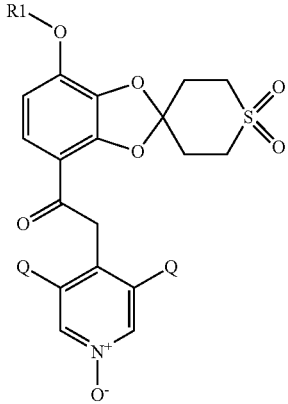
(I)

wherein $R_1$ is selected from $CHF_2$ and $CF_3$, and Q is selected from chloro, bromo, and fluoro, comprising each of steps (2a), (2b), (3), and (4) as defined in claim 1, and subsequently oxidizing the resulting compound.

12. A method for preparing a compound of formula (I)

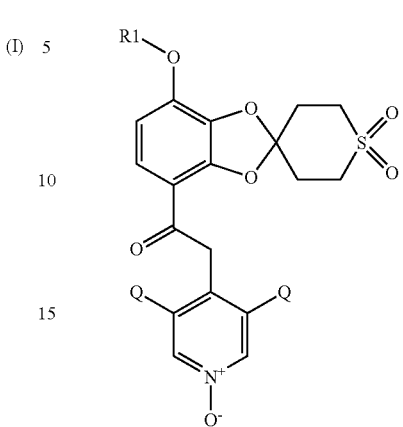
(I)

wherein $R_1$ is selected from $CHF_2$ and $CF_3$, and Q is selected from chloro, bromo, and fluoro, comprising each of the following steps:

(2a) reacting a compound of formula (IV)

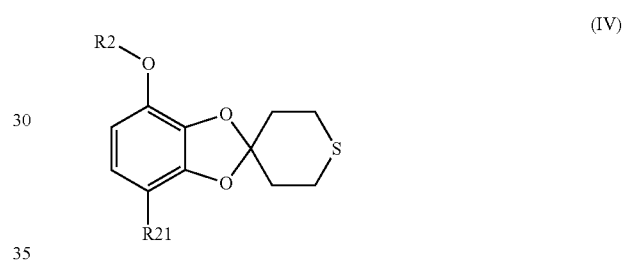
(IV)

with an aromatic or aliphatic thiol to form a compound of formula (VI)

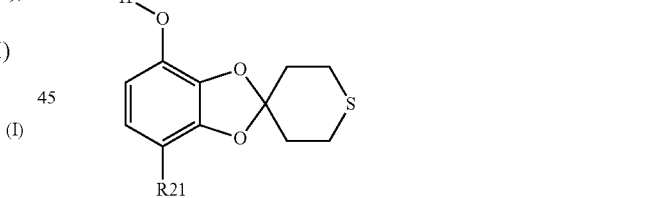
(VI)

wherein $R_{21}$ is $C(O)CH_3$ (2b+3) reacting the compound of formula (VI) with a difluorocarbene source in a polar solvent in the presence of a base, to form a compound of formula (IX)

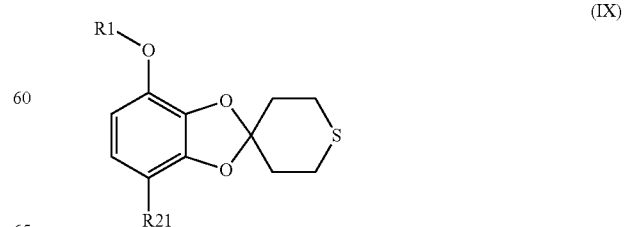
(IX)

wherein $R_1$ and $R_{21}$ are as defined above; and (4) reacting the compound of formula (IX) with a pyridine compound of formula (X)

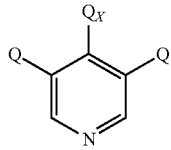

(X)

wherein Q is as defined above and $Q_x$ is selected from chloro, bromo, fluoro, and iodo to form a compound of formula (XI);

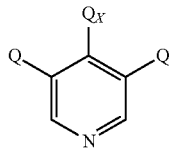

(X)

wherein $R_1$ and Q are as defined above;
subsequently oxidizing the resulting compound.

13. The method according to claim 12, wherein the reaction in step (2b+3) is conducted in a solvent selected from NMP (N methylpyrolidone), DMI (1,3-dimethyl-2-imidazolidinone), DMSO (dimethyl sulfoxide), EtOAc (ethyl acetate), MeCN (acetonitrile), THF (tetrahydrofuran), ethanol, methanol, water, and mixtures thereof, and in the presence of a base, selected from $K_2CO_3$, $Na_2CO_3$, $KHCO_3$, $NaHCO_3$, $Cs_2CO_3$, TEA (triethylamine), tert-BuOLi (lithium tert butoxide), sodium methoxide, sodium ethoxide, DIPEA (N,N-diisopropylethylamine), KOH, NaOH, and LiOH.

14. The method according to claim 12, wherein the difluorocarbene source of reaction in step (2b+3) is selected from sodium chloro-difluoroacetate, diethyl bromodifluoromethylphosphonate, chlorodifluoromethyl phenylsulfone, and 2-chloro-2,2-difluoroacetophenone.

15. An intermediate compound of formula (VII),

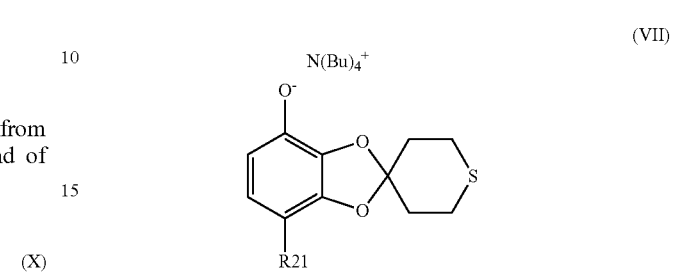

(VII)

wherein $R_{21}$ is $C(O)CH_3$.

16. An intermediate compound of formula (IX),

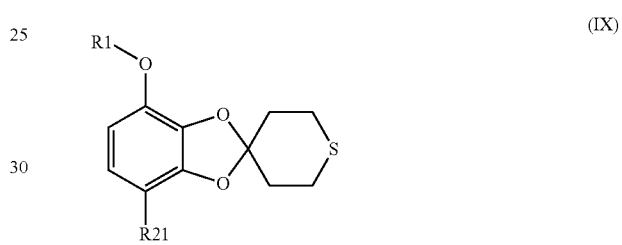

(IX)

wherein $R_1$ is selected from $CHF_2$ and $CF_3$, and $R_{21}$ is $C(O)CH_3$.

* * * * *

UNITED STATES PATENT AND TRADEMARK OFFICE
CERTIFICATE OF CORRECTION

PATENT NO. : 11,370,799 B2  Page 1 of 1
APPLICATION NO. : 16/062760
DATED : June 28, 2022
INVENTOR(S) : Dahl et al.

It is certified that error appears in the above-identified patent and that said Letters Patent is hereby corrected as shown below:

In the Claims

At Claim 12 at Column 37, Lines 15-24, delete the following chemical structure:

"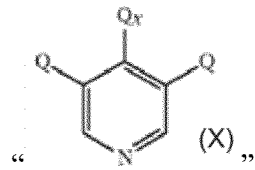"

And insert the following chemical structure in its place:

-- 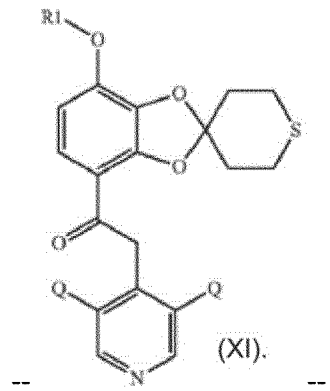 --

Signed and Sealed this
Twenty-fifth Day of October, 2022

Katherine Kelly Vidal
*Director of the United States Patent and Trademark Office*